United States Patent
Nakagawa

(10) Patent No.: US 8,235,894 B2
(45) Date of Patent: Aug. 7, 2012

(54) EMOTIONAL STATE DETERMINATION METHOD

(75) Inventor: Masahiro Nakagawa, Niigata (JP)

(73) Assignee: Nagaoka University of Technology, Niigata (JP)

(*) Notice: Subject to any disclaimer, the term of this patent is extended or adjusted under 35 U.S.C. 154(b) by 1558 days.

(21) Appl. No.: 11/681,388

(22) Filed: Mar. 2, 2007

(65) Prior Publication Data

US 2007/0202477 A1    Aug. 30, 2007

Related U.S. Application Data

(63) Continuation of application No. PCT/JP2005/016037, filed on Sep. 1, 2005.

(30) Foreign Application Priority Data

Sep. 2, 2004 (JP) ................................ 2004-255250
Feb. 28, 2005 (JP) ................................ 2005-054004

(51) Int. Cl.
*A61B 5/00* (2006.01)
*A61B 5/1455* (2006.01)
*G09B 19/00* (2006.01)

(52) U.S. Cl. ......... 600/300; 600/323; 600/408; 434/236

(58) Field of Classification Search .................. 600/300, 600/310, 322–323, 328, 340, 408; 356/41; 434/236

See application file for complete search history.

(56) References Cited

U.S. PATENT DOCUMENTS

| | | | |
|---|---|---|---|
| 5,504,841 A | 4/1996 | Tani | |
| 5,601,090 A * | 2/1997 | Musha | ........................ 600/544 |
| 5,803,909 A | 9/1998 | Maki et al. | |
| 6,128,517 A | 10/2000 | Maki et al. | |

(Continued)

FOREIGN PATENT DOCUMENTS

JP    06-014908    1/1994

(Continued)

OTHER PUBLICATIONS

Hoshi et al., "Dynamic multichannel near-infrared optical imaging of human brain activity", American Physiological Society, 0161-7567, 2003.*

(Continued)

*Primary Examiner* — Eric Winakur
*Assistant Examiner* — Chu Chuan (JJ) Liu
(74) *Attorney, Agent, or Firm* — Benesch, Friedlander, Coplan & Aronoff LLP

(57) ABSTRACT

The invention provides an emotional state determination method capable of quantitatively and accurately measuring an emotional state of a human being without requiring a special measuring environment. At least one of oxy-hemoglobin densities and deoxy-hemoglobin densities in blood of a plurality of measurement regions of a human brain cortex of a subject 1 are measured in time series, respectively, using a near-infrared spectroscopy. Then, cross-correlation coefficients of plural sets of time-variable change data are computed for each time (for each sampling period). Each of the plural sets of the time-variable change data comprises two of the time-variable change data which are selected by permutations and combinations from among at least one of the time-variable change data on the measured oxy-hemoglobin densities and the time-variable change data on the measured deoxy-hemoglobin densities. Then, by analyzing time-variable change patterns of the computed cross-correlation coefficients of the plural sets of the time-variable change data using a predetermined determination method, the emotional state of the subject is quantitatively measured.

17 Claims, 9 Drawing Sheets

U.S. PATENT DOCUMENTS

| | | | |
|---|---|---|---|
| 6,240,309 | B1 | 5/2001 | Yamashita et al. |
| 6,282,438 | B1 | 8/2001 | Maki et al. |
| 6,640,133 | B2 * | 10/2003 | Yamashita et al. ............ 600/476 |
| 6,657,183 | B2 * | 12/2003 | Yamamoto et al. ............. 356/41 |
| 6,901,284 | B1 | 5/2005 | Maki et al. |
| 7,047,149 | B1 | 5/2006 | Maki et al. |
| 7,186,217 | B2 | 3/2007 | Kawasaki |
| 7,206,622 | B2 | 4/2007 | Eda et al. |
| 2002/0103428 | A1 | 8/2002 | deCharms |
| 2003/0139654 | A1 * | 7/2003 | Kim et al. .................... 600/300 |
| 2004/0039267 | A1 | 2/2004 | Kawasaki et al. |
| 2004/0152060 | A1 | 8/2004 | Ando et al. |
| 2005/0177033 | A1 | 8/2005 | Kawasaki |

FOREIGN PATENT DOCUMENTS

| | | |
|---|---|---|
| JP | 06337852 | 6/1994 |
| JP | 08212275 | 8/1996 |
| JP | 08235351 | 9/1996 |
| JP | 2001-346780 | 12/2001 |
| JP | 2003-265446 | 9/2003 |
| JP | 2004-049510 | 2/2004 |
| JP | 2004-184402 | 7/2004 |
| JP | 2004-194924 | 7/2004 |
| JP | 2004-292981 | 10/2004 |

OTHER PUBLICATIONS

Sato, Takahiro and Nakagawa, Masahiro, "Emotion Quantification Using Fractal Dimension Analysis", Technical Report Office HIP2002-45, pp. 13-18 (2002).

Koizumi, et al., "Cerebral Function Measurement Using Optical Topography," Keisoku to Seigyo (Measurement and Control) Magazine, May 2003 Issue, No. 5, vol. 42, Japan.

Tamura, "Cerebral Function Measurement Using Infared Ray—Foundation thereof and Potentiality of Optical CT," Keisoku to Seigyo (Measurement and Control) Magazine, May 2003 Issue, No. 5, vol. 42, Japan.

* cited by examiner (Left Head Portion)

(Right Head Portion)

EMOTIONAL STATE DETERMINATION METHOD

TECHNICAL FIELD

The present invention relates to a method of quantitatively measuring an emotional state or emotional information (including a feeling and a will) and determining the emotional state or the emotional information. More specifically, the invention relates to a method of measuring time-variable changes of hemoglobin densities in blood in a plurality of measurement regions of a human brain cortex, and quantitatively determining the emotional state such as "joy, anger, sadness, or relaxation", based on results of the measurement.

BACKGROUND ART

Japanese Patent Publication No. 08-103434 (Patent No. 3359756) (referred to as Patent Document 1) discloses a technique in which amounts of change of oxy-hemoglobin densities and amounts of change of deoxy-hemoglobin densities in blood in a plurality of measuring regions of a human brain cortex of a subject are measured, results of the measurement are displayed on a display device, thereby obtaining biological information.

Japanese Patent Publication No. 09-19408 (referred to as Patent Document 2) discloses a technique in which oxy-hemoglobin densities in blood in a plurality of measurement regions of a human brain cortex of a subject are measured, auto-correlation and cross-correlation functions of time-variable changes in relative change amounts of the densities are computed, and a topography image is prepared from the correlation functions at individual measurement points. When the technique disclosed in this publication is used, a local biological function may be measured from the topography image.

In a technique disclosed in Japanese Patent Publication No. 09-149894 (Patent No. 3543453) (referred to as Patent Document 3), and deoxy-hemoglobin densities in blood in a plurality of measurement regions of a subject are measured, thereby obtaining measurement signals. Then, in this technique, a feature parameter is computed from each measurement signal. By determining whether a standard deviation of the feature parameter and an average value of the feature parameter belong to a distribution (a measurement region) of a standard deviation of predetermined reference data and an average value of the predetermined reference data, a brain function activity is measured. This publication shows that a neural network is employed as a method of the determination.

Japanese Patent Publication No. 11-311599 (referred to as Patent Document 4) discloses a specific optical measurement technique that may be employed when auto-correlation and cross-correlation functions of time-variable changes in relative change amounts of oxy-hemoglobin densities in blood in a plurality of measurement regions of a human brain cortex of a subject are computed, and a topography image is prepared from the correlation functions at individual measurement points, as in Patent Document 2.

Japanese Patent Publication No. 2000-237194 (referred to as Patent Document 5) discloses a specific technique related to the techniques disclosed in Patent Documents 2 and 4, which is employed when a result of measurement is displayed on a display device.

Further, WIPO International Publication No. WO2002-32317 (Patent Document 6) discloses a technique in which a time-variable change amount of a hemoglobin density is displayed on display means in the form of a graph associated with a positional relationship between optical irradiation means and optical detection means.

Japanese Patent Publication No. 2003-365445 (referred to as Patent Document 7) discloses a technique in which a ratio of a deoxy-hemoglobin density to an oxy-hemoglobin density is measured, and whether a mammal is stressed or relaxed is determined from a result of the measurement.

Japanese Patent Publication No. 2004-229948 (referred to as Patent Document 8) discloses a technique in which, by analyzing a change rate of a hemoglobin density, information on a degree of density of a subject is obtained, thereby determining a condition at a time of learning.

Japanese Patent Publication No. 2004-184402 (referred to as Patent Document 9) describes an appropriate relationship among a measurement period of a hemoglobin density, a task supplied to a subject, and a rest supplied to the subject.

Japanese Patent Publication No. 2004-170958 (referred to as Patent Document 10) proposes a technique in which at least a deoxy-hemoglobin amount in blood in a measurement region of a subject is measured in time series, and a learning level of work by the subject is determined from time-variable change data of the deoxy-hemoglobin amount.

Japanese Patent Publication No. 2004-194924 (referred to as Patent Document 11) discloses a technique of quantitatively measuring a brain function including emotion using an electroencephalogram.

Two documents propose a technique in which using near-infrared spectroscopy, a change in a brain blood flow caused by brain activity is observed, and a brain active region and a temporal variation of the brain activity are thereby measured. [Nonpatent Document 1: Mamoru Tamura, "Brain Function Measurement Using Near-infrared Light", Journal of the Society of Instrument and Control Engineers, Vol. 42, No. 5, pp. 396-401, (2003.5) and Nonpatent Document 2: Hideaki Koizumi, Atsushi Maki, Takeshi Yamamoto, Hideo Kawaguchi, Fumio Kawaguchi, Noriyoshi Ichikawa, "Brain Function Measurement Using Optical Topography", Journal of the Society of Instrument and Control Engineers, Vol. 42, No. 5, pp. 402-407, (2003.5)].

Patent Document 1: Japanese Patent Publication No. 08-103434
Patent Document 2: Japanese Patent Publication No. 09-19408
Patent Document 3: Japanese Patent Publication No. 09-149894
Patent Document 4: Japanese Patent Publication No. 11-311599
Patent Document 5: Japanese Patent Publication No. 2000-237194
Patent Document 6: WIPO International Publication WO2002-32317
Patent Document 7: Japanese Patent Publication No. 2003-365445
Patent Document 8: Japanese Patent Publication No. 2004-229948
Patent Document 9: Japanese Patent Publication No. 2004-184402
Patent Document 10: Japanese Patent Publication No. 2004-170958
Patent Document 11: Japanese Patent Publication No. 2004-194924
Nonpatent Document 1: Mamoru Tamura, "Brain Function Measurement Using Near-infrared Light", Journal of the Society of Instrument and Control Engineers, Vol. 42, No. 5, pp. 396-401, (2003.5)
Nonpatent Document 2: Hideaki Koizumi, Atsushi Maki, Takeshi Yamamoto, Hideo Kawaguchi, Fumio Kawaguchi, Noriyoshi Ichikawa, "Brain Function Measurement Using Optical Topography", Journal of the Society of Instrument and Control Engineers, Vol. 42, No. 5, pp. 402-407, (2003.5)

DISCLOSURE OF THE INVENTION

Problem to be Solved by the Invention

In order to quantitatively measure an emotional state of a human being using an electroencephalogram as with the technique described in Patent Document 11, however, it is necessary to prepare for an environment suited to measurement of an electroencephalogram. This technique is not therefore practical. In fact, various studies have been made on obtaining human biological information (including brain function information) based on a hemoglobin density, as described in Patent Documents 1 through 10 and Nonpatent Documents 1 and 2. However, just by computing cross-correlation functions of time-variable change amounts of hemoglobin densities as with conventional arts disclosed in Patent Documents 2, 4, and 5, and just by displaying a result of the computation as a topography image, an emotional state of a human being such as the "joy, anger, sadness, or relaxation" cannot be measured quantitatively and accurately. Still more, just by making determination based on a ratio of a deoxy-hemoglobin density to an oxy-hemoglobin density alone, as with the technique disclosed in Patent Document 7, an emotional state of a human being including a change in the joy, anger, sadness or relaxation of the human being cannot be known.

An object of the present invention is to provide an emotional state determination method capable of quantitatively and accurately measuring an emotional state (including a will) of a human being, without requiring a special measuring environment.

Means for Solving the Problem

In an emotional state determination method of the present invention, at least one of oxy-hemoglobin densities and deoxy-hemoglobin densities in blood of a plurality of measurement regions of a human brain cortex of a subject are measured in time series, respectively, using a near-infrared spectroscopy. Then, based on at least one of time-variable change data on the measured oxy-hemoglobin densities and time-variable change data on the measured deoxy-hemoglobin densities, an emotional state of the subject is determined. Specifically, in the method of the present invention, a reference data collection step, a judging condition determination step, an evaluation data collection step, and a determination step are implemented.

In the reference data collection step, at least one of time-variable change data on the oxy-hemoglobin densities and time-variable change data on the deoxy-hemoglobin densities are first measured for the respective measurement regions of the subject, under each of plural types of conditions that influence emotion. Then, computation of cross-correlation coefficients of plural sets of the time-valuable change data is performed for each unit time (for each sampling period). Each of the plural sets comprises two of the time-valuable change data which are selected by permutations and combinations from among the measured at least one of time-variable change data on the oxy-hemoglobin densities and the time-variable change data on the deoxy-hemoglobin densities. Then, a plurality of time-variable change patterns of the computed cross-correlation coefficients with respect to the plural sets of the time valuable change data are collected, as a plurality of reference data.

"The plural types of conditions that influence emotion" are a "condition of joy", a "condition of anger", a "condition of sadness", and a "condition of relaxation (relaxation)", for example. Accordingly, these conditions are intentionally created, and collection of the reference data is performed in each of these conditions The "at least one of time-variable change data on the oxy-hemoglobin densities and time-variable change data on the deoxy-hemoglobin densities" includes the "time-variable change data on the oxy-hemoglobin densities and the time-variable change data on the deoxy-hemoglobin densities", only the "time-variable change data on the oxy-hemoglobin densities", and only the "time-variable change data on the deoxy-hemoglobin densities". The number of the measurement regions may be two or more. When the two or more measurement regions are present, it is theoretically possible to measure necessary data. However, in order to increase measurement accuracy to a certain level, it is preferable to perform measurement in four more measurement regions. Then, the "plural sets of the time-variable change data selected by permutations and combinations" are defined as follows. Assume that both of the oxy-hemoglobin densities and the deoxy-hemoglobin densities are measured when the number of the measurement regions is n (in which n is a positive integer). In this case, when the plural sets of the data is set to m sets, m becomes the number obtained by $m={}_{2n}C_2$. When n is set to 24, m becomes 1128. Accordingly, when the reference data on the four conditions of joy, anger, sadness, and relaxation is collected in advance, 4×1128 types of the reference data will be collected. When one of the oxy-hemoglobin densities and the deoxy-hemoglobin densities are measured, m becomes the number obtained by $m={}_nC_2$. In this case, the number of the types of the reference data to be collected in advance becomes $(n-1)/[2(2n-1)]$ times the types of the reference data when both of the oxy-hemoglobin densities and the deoxy-hemoglobin densities are measured. Incidentally, a will of the subject (will of Yes or No) may be included in the "emotion".

"Computation of a cross-correlation coefficient for each unit time" means computation of the cross-correlation coefficient between two data sections obtained within the unit time that has been determined in advance. The following expression, for example, may be employed as an expression that uses the cross-correlation coefficient:

$$c_{j,k}(t) = \frac{\sum_{\tau=t} x_j(\tau) x_k(\tau)}{\sqrt{\sum_{\tau=t} x_j^2(\tau)} \sqrt{\sum_{\tau=t} x_k^2(\tau)}} \quad \text{[Expression 1]}$$

In the above expression, $x_j(\tau)$ is an oxygenated (deoxygenated) hemoglobin density change amount in a channel j at a time $\tau$. The time $\tau$ is a time range in which the cross-correlation coefficient is computed.

When the cross-correlation coefficient is computed at the same time (in real time) as obtaining the data, the unit time may be set to be the same as the sampling period of the data. When the unit time is set to be the same as the sampling period, the number of computations becomes the largest. Actually, the data is obtained in advance. Then, computation of the cross-correlation coefficient is later performed on the basis of the predetermined unit time. Then, by a plurality of cross-correlation coefficients obtained by these results of computation, one "cross-correlation coefficient time-variable change pattern" on one set of different two of the data can be obtained. As described before, when m is set to 1128, 4×1128 "cross-correlation coefficient time-variable change patterns" will be obtained. These patterns are stored as the reference data constituted by collective data of the results of computation.

In the judging condition determination step, a judging condition necessary for determining the emotional state of the subject by a predetermined determination method is determined from the plurality of reference data obtained in the reference data collection step. When determination is made by using a linear mapping determination method as the determination method, for example, the judging condition is constituted by an emotion matrix of a linear mapping and a bias vector, defined based on the reference data. These are an emotion matrix $a_{i,j}$ and a bias vector $d_i$ ($1 \leq i \leq 4$, $1 \leq j \leq 1128$) shown in FIG. 9, which will be described later, and are determined by a minimum square method over a reference segment. When a neural network is employed as the determination method, the judging condition is the one obtained when a required output value is given to an output layer of the neural network in advance in the reference segment and learned.

In the evaluation data collection step, at least one of the time-variable change data on the oxy-hemoglobin densities and the time-variable change data on the deoxy-hemoglobin densities is obtained for the respective measurement regions of the subject under a predetermined condition. Then, cross-correlation coefficients of the plural sets of the time-variable change data are computed for the each unit time. Each of the plural sets comprises two of the time-variable change data which are selected by permutations and combinations from among the obtained at least one of the time-variable change data on the oxy-hemoglobin densities and the time-variable change data on the deoxy-hemoglobin densities. Then, a plurality of time-variable change patterns of the computed cross-correlation coefficients with respect to the plural sets of the data are collected as a plurality of evaluation data. "Under the predetermined condition" means under the condition, such as the one under which a film is seen, which influences the emotion of the subject. Computation of the cross-correlation coefficients and collection of the time-variable change patterns on the cross-correlation coefficients in this evaluation data collection step are the same as the computation and the collection of the patterns in the reference data collection step described before.

Then, in the determination step, the judging condition determined in the condition determination step and the plurality of evaluation data are input, and the emotional state of the subject (including the will) is quantitatively determined by the predetermined determination method described before.

In a conventional art, the cross-correlation coefficients are not computed for each unit time, as in the present invention. In the conventional art, an overall cross-correlation coefficient between two hemoglobin density time-variable change amount data obtained from two measurement regions is computed as a constant rather than a variable that depends on time. Then, based on a result of the computation, biological information is obtained. For this reason, according to the conventional art, some change in the biological information may be vaguely known from a hemoglobin density time-variable change. However, in the biological information obtained by the conventional art, a change in human emotion (of joy, anger, sadness, or relaxation) cannot be determined with a high recognition accuracy. Then, as a result of various studies by an inventor, the following was found. When reference data is collected and evaluation data is collected, assume that cross-correlation coefficients of plural sets of data, which vary over time, are computed for each unit time. Each of the plural sets comprises two of the time-variable change data which are selected by permutations and combinations from at least one of oxy-hemoglobin density time-variable change data and deoxy-hemoglobin density time-variable change data measured for respective measurement regions of a subject. Then, assume that time-variable change patterns of the cross-correlation coefficients are obtained, and using these time-variable change patterns of the cross-correlation coefficients, an emotional state is determined. Then a change in the emotional state can be determined with a high recognition accuracy. The present invention is obtained as a result of trial and error. According to the present invention, the average recognition accuracy of the emotional state (including consciousness) can be approximately doubled (from 50% to 90%), compared with the conventional art. The method of the present invention is not limited to a case where plural types of emotional states are always determined, and is naturally applied to a case where at least one emotional state is determined, as well. The "emotional state" may of course include a will of the subject such as "Yes" or "No" and will information such as "up", "down", "left", or "right".

It is not necessary to make hemoglobin density measurement in a special environment that prevents inclusion of extraneous noise, such as the one where an electroencephalogram is measured. For this reason, quantitative measurement of the emotional state of a human being may be simply and easily made. When the near-infrared spectroscopy in particular is used, the measurement may be made without passing a current through the human brain cortex. Thus, the emotional state of the human being may be obtained without considering an influence on a brain.

When each of the above steps is executed, the emotional state may be quantitatively measured with comparatively simple and easy steps. Further, in view of a structure of a measuring device, the subject is hardly placed under restraint. Accordingly, there is an advantage that ideal measurement of emotion may be performed.

As the sampling period described before becomes longer, recognition accuracy of the emotion will decrease. Practically, it is preferable that the unit time is one second or less. The measurement accuracy may be increased more in the greater number of the measurement regions than the smaller number of the measurement regions. In order to ensure the accuracy of a certain level, it is preferable that four or more measurement regions are provided.

BEST MODE FOR CARRYING OUT THE INVENTION

Figure 1:
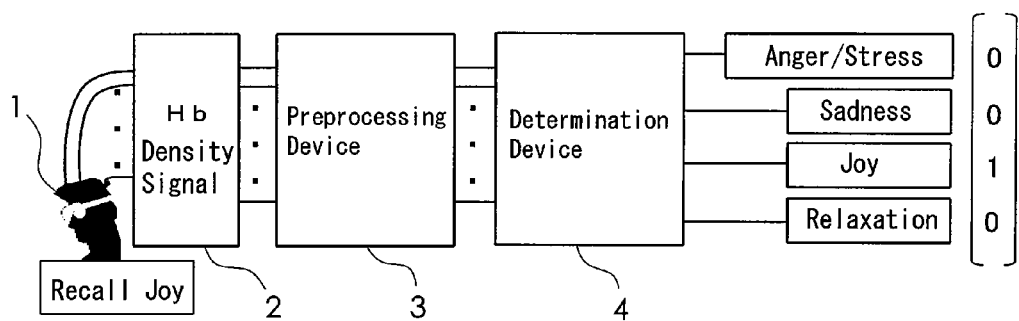
FIG. 1 is a diagram schematically showing a configuration of an example of a emotion information measuring device that carries out an emotional state determination method of the present invention.
Figure 2:
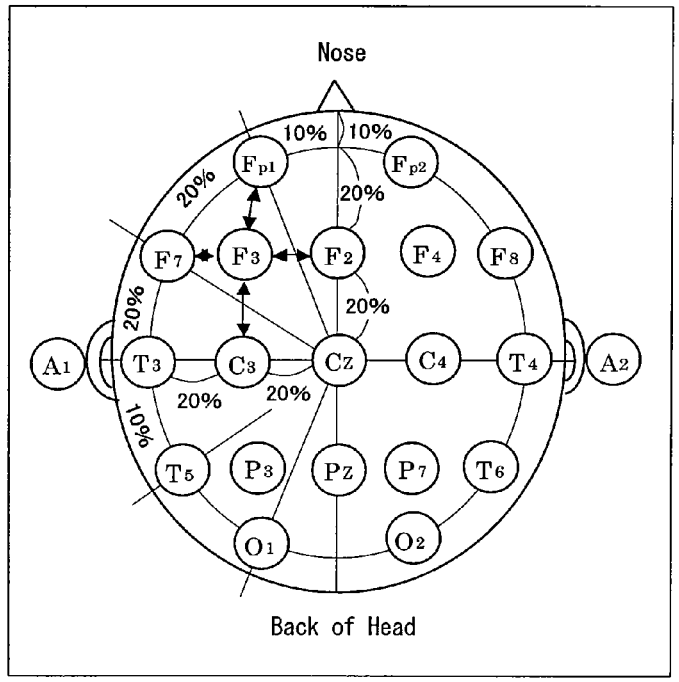
FIG. 2 is a diagram showing an example of measurement points.
Figure 3:
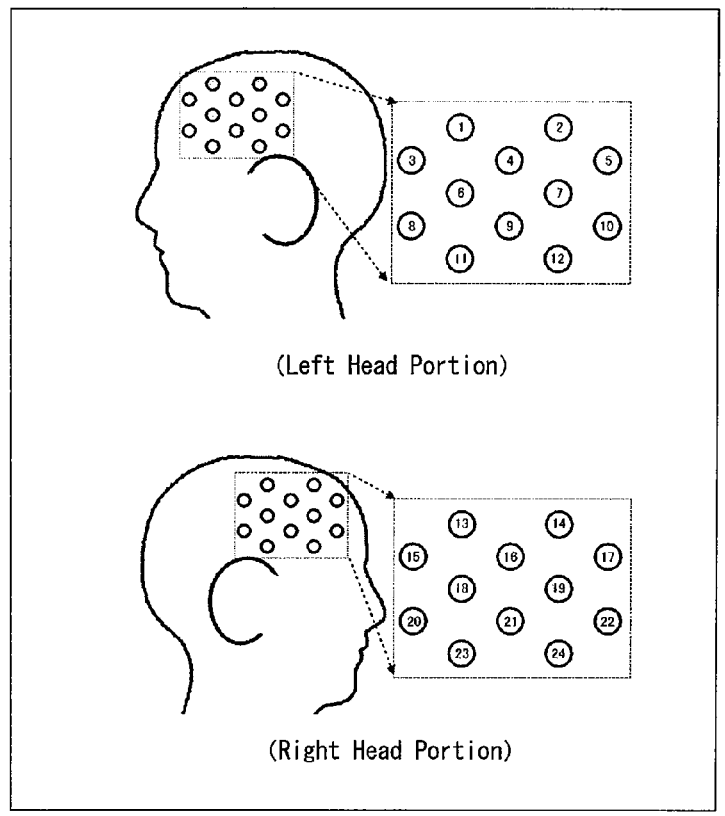
FIG. 3 is a diagram showing measurement points in an embodiment and Experiment 2.

An embodiment of the present invention will be described below with reference to drawings. FIG. 1 is a diagram schematically showing an example of a configuration of an emotion information measuring device that carries out an emotional state determination method of the present invention. Reference numeral 1 indicates a subject whose emotional state is to be measured. Reference numeral 2 indicates a hemoglobin density measuring device that measures hemoglobin densities in blood in a plurality of measurement regions of a human brain cortex of the subject 1 in time series, respectively, using a near-infrared spectroscopy. As such a measuring device, an optical topography system ETG-100 (trademark) manufactured and sold by Hitachi Medical Corporation, for example, may be employed. On the head of the subject 1, a plurality of output probes each of which outputs a near-infrared ray and a plurality of light-receiving probes (channels) each of which receives the near-infrared ray that has passed through the human brain cortex are arranged in measurement locations as shown in FIG. 2, respectively, for example. In this embodiment, a channel constituted by a pair of an output probe and a light-receiving probe is arranged on each of 24 measurement regions of the head of the subject 1, as shown in FIG. 3. A portion enclosed by a circle in FIG. 3 shows a measurement location, while a number enclosed by the circle indicates the channel. These measurement regions (measurement locations) are tentatively determined. A sampling frequency of 10 [Hz] is used, and no special processing such as filtering is not performed on a resulting signal. Using the channels in these 24 measurement regions, the hemoglobin density measuring device 2 outputs 24 types of hemoglobin density measurement signals each indicating an oxy-hemoglobin density in each measurement region and 24 types of hemoglobin density measurement signals each indicating a deoxy-hemoglobin density in each measurement region. These signals are input to a preprocessing device 3, stored in internal storage means, and then, preprocessed.

In the preprocessing device 3, preprocessing for obtaining reference data is first carried out (in a reference data collection step). Then, processing for obtaining evaluation data is carried out (in an evaluation data collection step).

Figure 4:
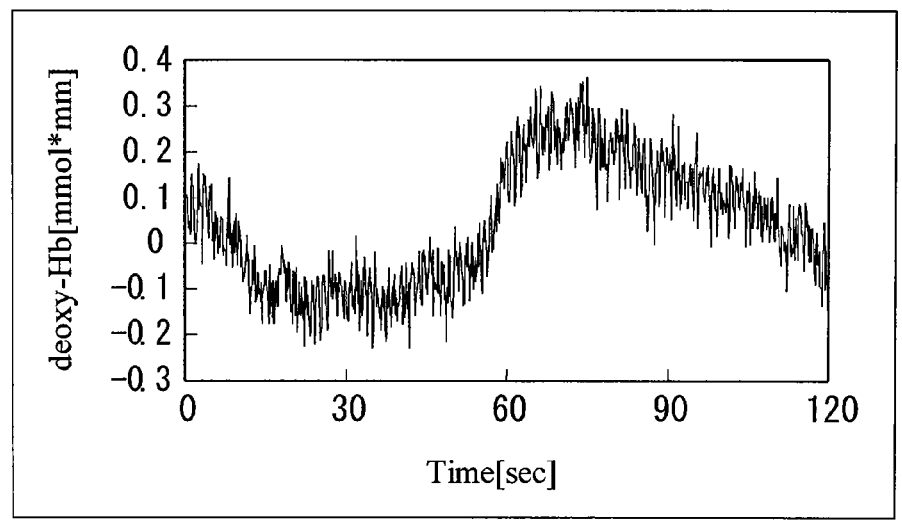
FIG. 4 is a graph showing an example of time-variable change data on a hemoglobin density (indicated by a hemoglobin density measurement signal) in a certain measurement region (channel).
Figure 5:
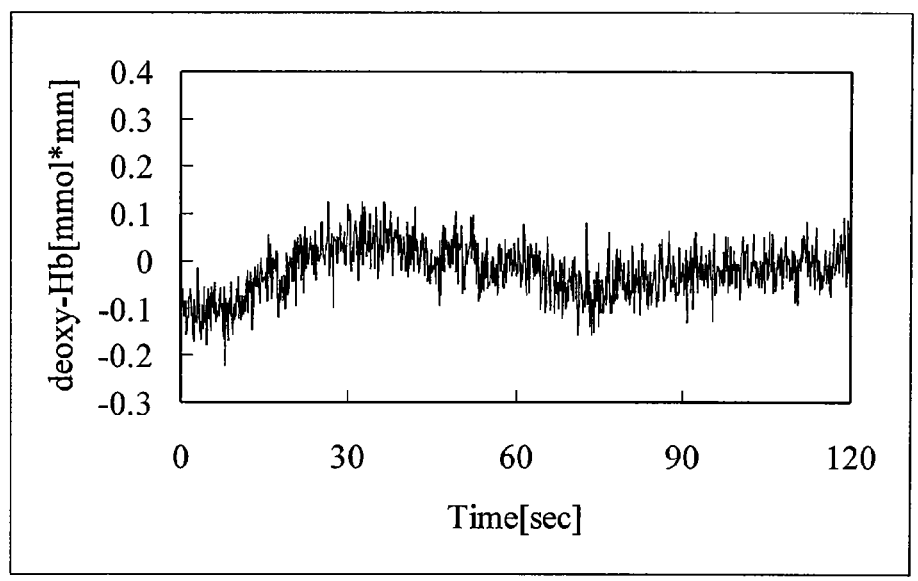
FIG. 5 is a graph showing an example of time-variable change data on a hemoglobin density (indicated by a hemoglobin density measurement signal) in other measurement region (channel).

In the reference data collection step, the subject is first made to recall four fundamental conditions of emotion, or "anger", "sadness", "joy" and "relaxation", independently. Then, in each of the conditions, time-variable change data on the oxy-hemoglobin densities (or the 24 oxy-hemoglobin density measurement signals) and time-variable change data on the deoxy-hemoglobin densities (or the 24 deoxy-hemoglobin density measurement signals), which have been measured for the respective 24 measurement regions of the subject, are obtained, and stored in the storage means within the preprocessing device 3. FIGS. 4 and 5 indicate examples of results of measurement in certain measurement regions (channels), respectively. More specifically, FIGS. 4 and 5 indicate examples of time-variable change data on the hemoglobin densities (hemoglobin density measurement signals). As seen from FIGS. 4 and 5, measurement of each hemoglobin density is performed for two minutes (120 seconds), in this embodiment. Since the sampling frequency is 10 [Hz], a sampling period is 0.1 seconds.

Figure 6:
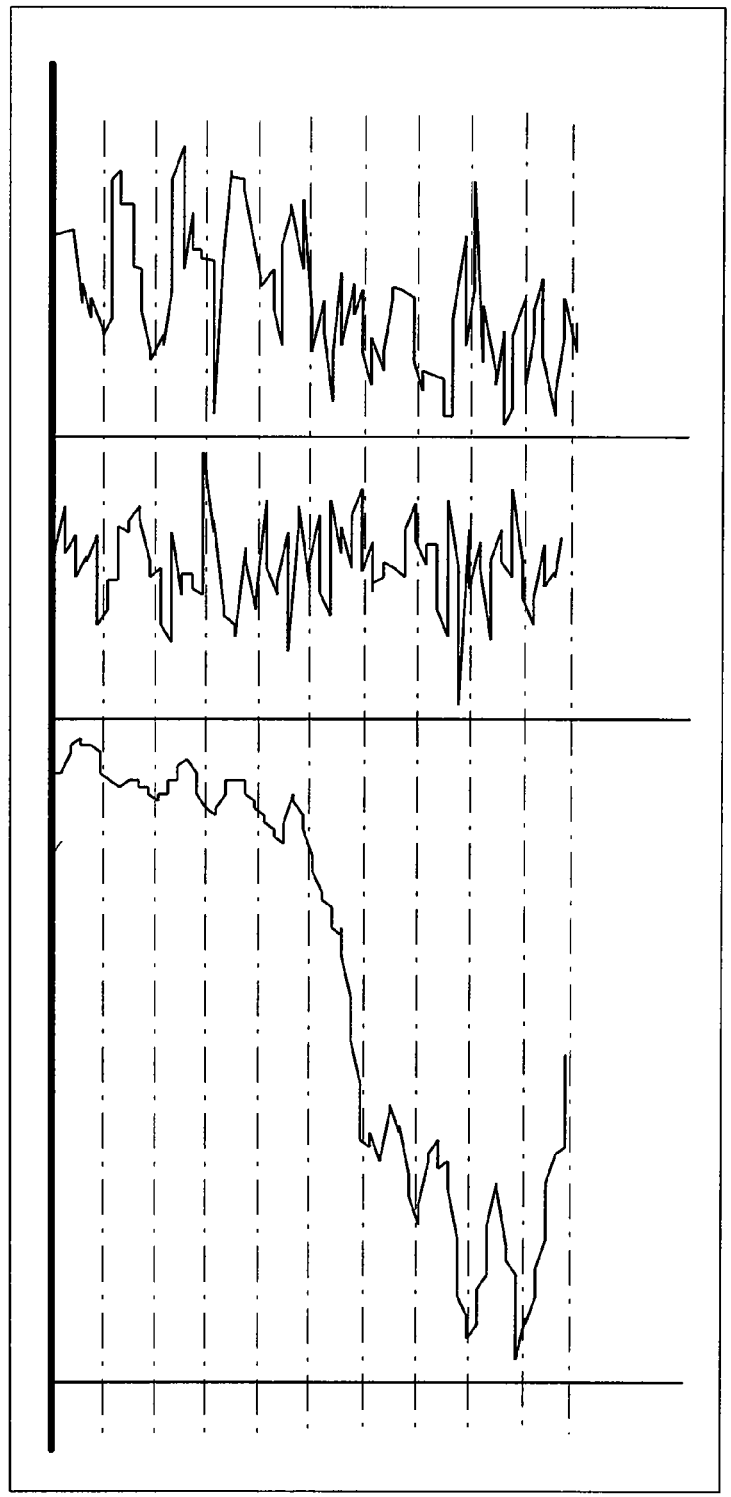
FIG. 6 is a diagram used for explaining a concept when a correlation coefficient between two different data is computed.
Figure 7:
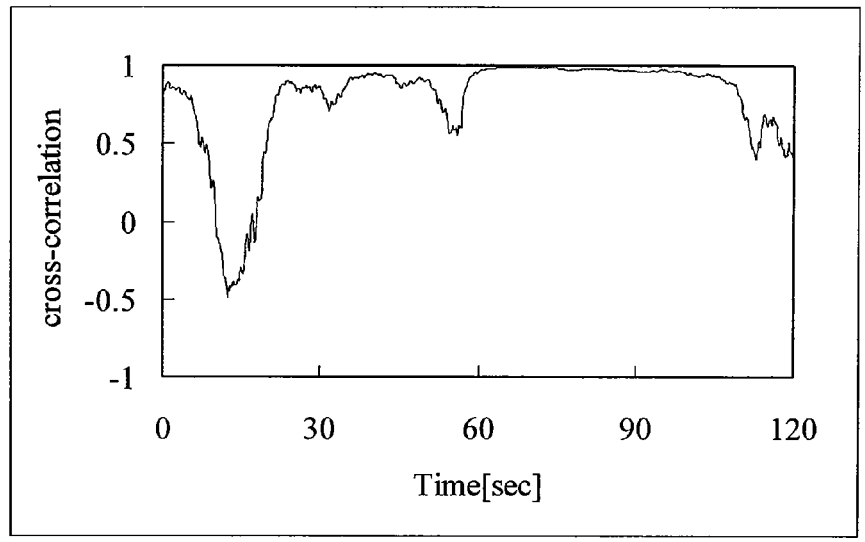
FIG. 7 is a graph showing an example of a time-variable change pattern of a cross-correlation coefficient between two different data.
Figure 8:
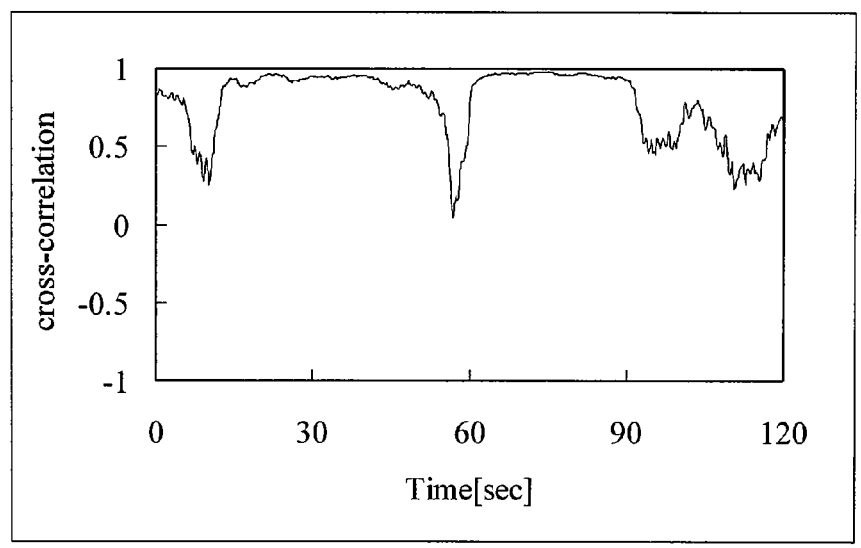
FIG. 8 is a graph showing an example of a time-variable change pattern of a cross-correlation coefficient between other two different data.

Next, a cross-correlation coefficient of each of 1128 ($_{48}C_2$) sets of two different data selected from among these 48 types of data by permutations and combinations is computed for each unit time (for example, the cross-correlation coefficient is computed for each 0.1 second, using time series data of the hemoglobin densities one second before and after a time of interest). In order to compute the cross-correlation coefficient between the two different data for each unit time, the cross-correlation coefficient of portions of the two data during a predetermined unit time is computed, for each predetermined unit time. Using the cross-correlation coefficients obtained by computing the cross-correlation coefficient of the two different data for each unit time, a time-variable change pattern of the cross-correlation coefficient of a set of the two different data is obtained. FIG. 6 is a graph used for explaining a concept when the cross-correlation coefficient of the two different data is computed. Referring to FIG. 6, two waveforms on an upper side indicate the data. Results of the computation of the cross-correlation coefficient of the two data at a predetermined time interval as shown in a chain line are plotted in the bottom, thereby obtaining the time-variable change pattern of the cross-correlation coefficient. Incidentally, in FIG. 6, in order to facilitate understanding, chain lines indicating time intervals are only partially shown. As clear from the pattern, the computation is actually performed at shorter time intervals. FIGS. 7 and 8 show examples of time-variable change patterns of cross-correlation coefficients of two sets of two different data, respectively. As seen from FIGS. 7 and 8, the time-variable change patterns of these cross-correlation coefficients show the time-variable changes of the cross-correlation coefficients over two minutes (120 seconds), respectively. Then, the cross-correlation coefficients are values that range from −1 to +1. As a coefficient value is closer to +1, it indicates that positive correlation is stronger. As the coefficient value is closer to −1, it indicates that negative correlation is stronger.

When the cross-correlation coefficient between channels j and k at a time t is indicated by a cross-correlation coefficient $c_{j,k}(t)$ between the channels placed on a measurement region, the cross-correlation coefficient is given by the following expression:

$$c_{j,k}(t) = \frac{\sum_{\tau=t} x_j(\tau)x_k(\tau)}{\sqrt{\sum_{\tau=t} x_j^2(\tau)} \sqrt{\sum_{\tau=t} x_k^2(\tau)}} \quad \text{[Expression 2]}$$

in which $x_j(\tau)$ is an oxygenated (deoxygenated) hemoglobin density change amount in the channel j at a time $\tau$. A range of a time range $\tau$ in which the cross-correlation coefficient is computed is set to 4 [sec] or less.

In this embodiment, the cross-correlation coefficients of the 1128 sets of two different data for each unit time in each of the four conditions of "anger", "sadness", "joy", and "relaxation" are computed. Accordingly, in this embodiment, 4×1128 of the "time-variable change patterns of the cross-correlation coefficients" are obtained in the reference data collection step. These patterns are stored in the storage means within the preprocessing device 3 as reference data constituted by collective data of results of the computation.

Next, the preprocessing device 3 executes a judging condition determination step. In this judging condition determination step, a judging condition necessary for determining the emotional state of the subject is obtained from the plurality of reference data obtained in the reference data collection step described before, using a predetermined determination method. In this embodiment, a determination device 4 makes determination using a linear mapping determination method as the determination method.

When the linear mapping determination method is used, an input vector $y=c_{i,j}$ ($1 \le i \le 4$, $1 \le j \le 1128$)(t) is linearly transformed into a four-dimensional vector $z=(z_1, z_2, z_3, z_4)$ using a linear mapping $A=a_{i,j}$ and a bias vector $d_i$ ($1 \le i \le 4$). These mapping and vectors are related as follows:

$$A = \begin{bmatrix} a_{1,1} & a_{1,2} & \cdots & a_{1,1128} \\ a_{2,1} & a_{2,1} & \cdots & a_{2,1128} \\ a_{3,1} & a_{3,1} & \cdots & a_{3,1128} \\ a_{4,1} & a_{4,1} & \cdots & a_{4,1128} \end{bmatrix}, \quad y(t) = \begin{bmatrix} c_{1,2}(t) \\ c_{1,3}(t) \\ \vdots \\ c_{46,48}(t) \\ c_{47,48}(t) \end{bmatrix} \quad \text{[Expression 3]}$$

$$A \cdot y(t) + d = z$$

in which d indicates the bias vector, and is actually expressed as $[d_1, d_2, d_3, d_4]$. A matrix A ($a_{1,1}$ to $a_{4, 1128}$) expressing the linear mapping corresponds to an emotion matrix in an emotion spectral analysis method. $a_{1,1}$ to $a_{1,1128}$, $a_{2,1}$ to $a_{2,1128}$ $a_{3,1}$ to $a_{3,1128}$ and $a_{4,1}$ to $a_{4,1128}$ are linear mappings obtained by the time-variable change patterns of the cross-correlation coefficients between the 1128 sets of the two reference data in one of a "condition of joy", a "condition of anger", a "condition of sadness", and a "condition of relaxation (or relaxation)", respectively. The constant vector d and the matrix A are determined in a following manner. The constant vector d and the matrix A are determined so that when the "anger" is recalled, for example, an output z as cross-correlation coefficients $C_{1,2}(t)$ to $C_{47,48}(t)$ of the reference data are input becomes (1,0,0,0), when the "sadness" is recalled, the output z as the cross-correlation coefficients of the reference data are input becomes (0,1,0,0), when the "joy" is recalled, the output z as the cross-correlation coefficients of the reference data are input becomes (0,0,1,0), when the "comfort (relaxation)" is recalled, the output z as the cross-correlation coefficients of the reference data are input becomes (0,0,0,1). Actually, the matrix A expressing the linear mapping and the bias vector d are determined so that a square error $e^2$ defined between a required output Zi and an actual output Zi(t) in the following expression, with respect to each emotion in a reference data segment, becomes minimum. In the following expression, T denotes time arranged in time series for reference data, and a sum of i denotes a sum of four types of emotions of the joy, anger, sadness, and relaxation.

$$\varepsilon^2 = \sum_{i=1}^{4} \sum_{t=0}^{T} (z_i(t) - Z)^2 \quad \text{[Expression 4]}$$

$$z_i(t) = \sum_{j=1}^{1128} a_{ij} y_j(t) + d_i \quad (1 \le i \le 4)$$

By minimizing the square error $\epsilon^2$ with respect to the linear mapping $a_{ij}$ and the bias vector $d_i$, the linear mapping $a_{ij}$ and the bias vector $d_i$ are determined.

The judging condition determined as described above is input to the determination device 4. Then, an evaluation data collection step is next executed. In this evaluation data collection step, time-variable change data on the oxy-hemoglobin densities and time-variable change data on the deoxy-hemoglobin densities are measured by the hemoglobin density measuring device 2 for the respective measurement regions of the subject under a predetermined condition (which is one of the conditions of the "anger", "sadness", "joy", and "relaxation"). Then, by the preprocessing device 3, the cross-correlation coefficients of plural sets of the two different data selected from among these measured time-variable change data by permutations and combinations are computed for each unit time. Then, cross-correlation coefficient time-variable change patterns of the plurality of sets of the two different data obtained by the computation are stored in storage means within the preprocessing device 3 as a plurality of evaluation data. Being under the predetermined condition means being under the condition, such as under the condition in which the subject is seeing a film, which influences emotion of the subject. Computation of the cross-correlation coefficients, collection of the cross-correlation coefficient time-variable change patterns, and the like in this evaluation data collection step are the same as the computation and collection of the patterns in the reference data collection step described before. Accordingly, even in this step, cross-correlation coefficients $y(t)=C_{1,2}(t)$ to $C_{47,48}(t)$ of the 1128 ($_{48}C_2$) sets of the two different data selected from among the 48 types of data (24 types of oxy-hemoglobin density measurement signals and 24 types of deoxy-hemoglobin density measurement signals) by the permutations and combinations are computed for each unit time (for each 0.1 second in this embodiment).

Figure 9:
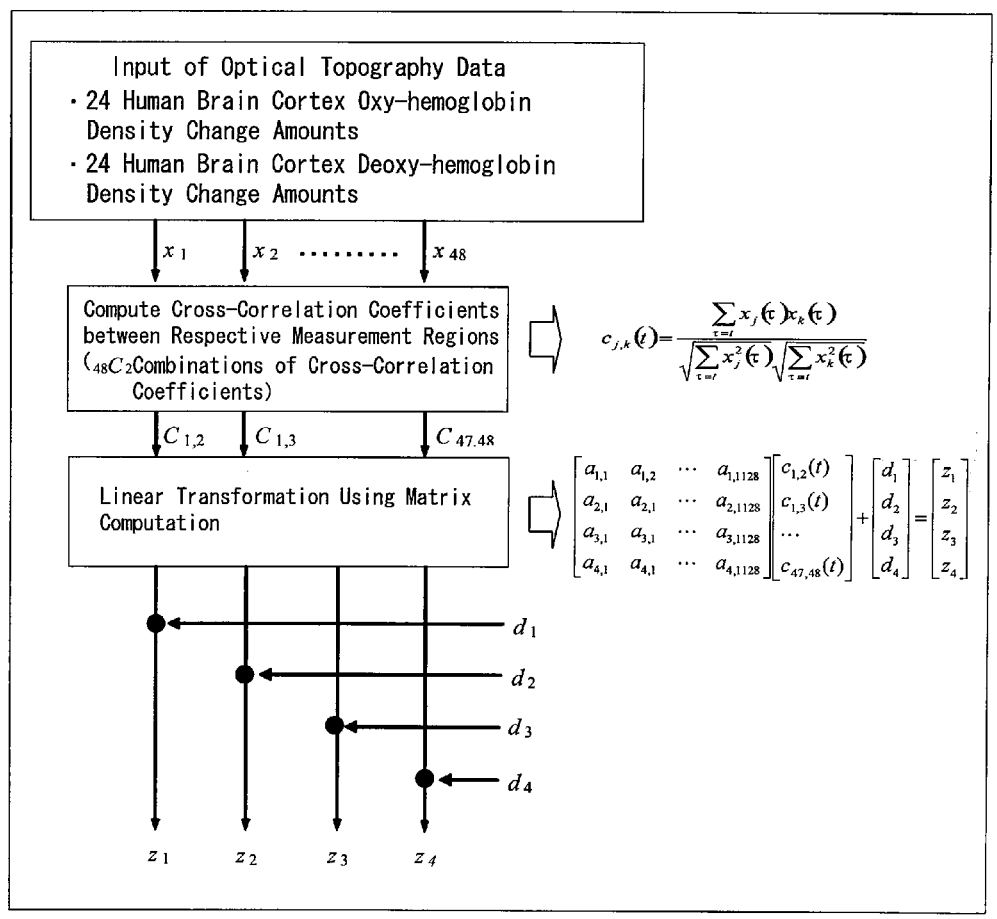
FIG. 9 is a flowchart showing flows of an evaluation data collection step and a determination step.

Next, the determination device 4 inputs the evaluation data $y(t)=C_{1,2}(t)$ to $C_{47,48}(t)$ into the expression described before, and linearly transforms the input vector y(t) to the four-dimensional vector $z=(z_1, z_2, z_3, z_4)$ using the linear mapping A. Magnitudes of these components indicate a level of a feature quantity corresponding to an emotional state. Thus, according to this embodiment, the judging condition is determined in advance based on reference data. Then, just by inputting evaluation data into the determination device 4, an emotional state may be quantitatively determined. FIG. 9 is a flowchart showing flows of the evaluation data collection step and the determination step.

Next, a result of an experiment conducted according to the embodiment described above will be explained.

[Experiment 1]

As the device that measures respective changes in oxy-hemoglobin densities and deoxy-hemoglobin densities on a human brain cortex using the near-infrared spectroscopy, the optical topography system ETG-100 manufactured by Hitachi Medical Corporation was used. Based on the 10-20 electrode system of the international federation in electroencephalogram measurement, single-electrode measurement using 10 points of Fp1, Fp2, F3, F4, T3, P3, P4, O1, O2 was made. The subjects are five men of 22 to 24 years old, who are healthy both in mind and body. The measurement was made in a condition where all of the subjects were at rest with their eyes closed. Only data measured from the subjects who have already experienced a plurality of measurements and have been used to the measurements was used. When the measurement was made, the measurement of four types of fundamental emotions of "anger", "sadness", "joy", and "relaxation" is informed to the subjects. The subjects are made to carry out mental training that causes the subjects to recall each emotional state, and then, the measurement was made by the following steps:

1. The subjects are informed to image one emotion and maintain the imaged state of the one emotion for approximately 10 minutes.

2. Approximately first three minutes are set to a preparation period for the subjects, during which no recording is performed.

3. Then, the recording of three to five minutes is performed, and this recording is stored as reference data used for learning (indicated by emotional state determination reference signals).

4. Then, recording of one to three minutes is performed, and this recording is used as evaluation data used for a test (indicated by emotional state measuring analysis signals).

5. After a rest of approximately five minutes, the procedure is returned to 1, and the next emotion is informed.

Figure 10:
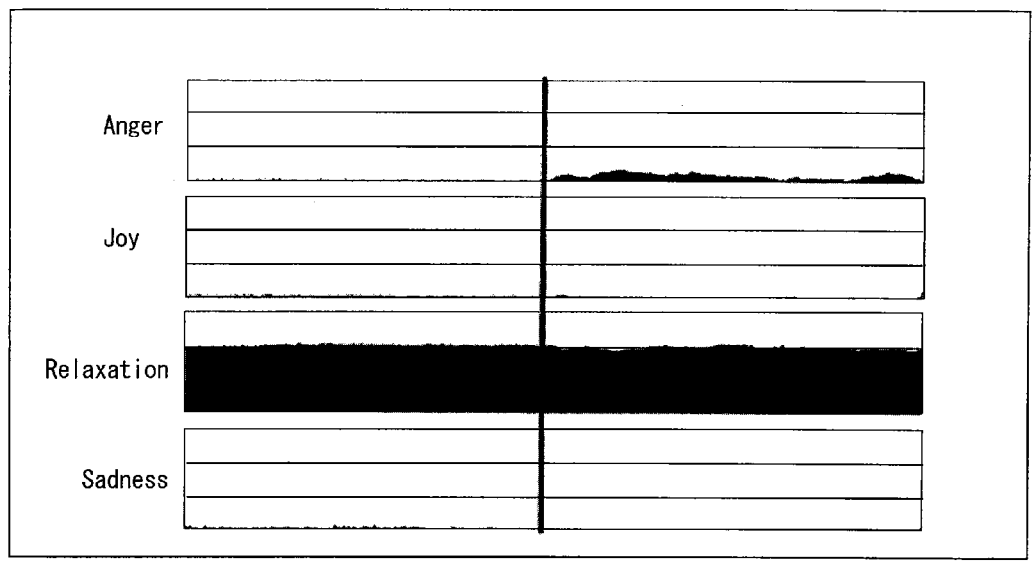
FIG. 10 is a diagram showing an example of a recognition accuracy in Experiment 1.

As the determination method, the linear mapping determination method was used. In the linear mapping determination method, a result of determination is obtained by using the linear mapping obtained from the reference data described in the above-mentioned embodiment and the cross-correlation coefficients (matrix computation results) obtained from the evaluation data. An example of a recognition accuracy of the signals (emotional state determination reference signals) indicating a "relaxed state" prepared for the experiment is shown in FIG. 10. Referring to FIG. 10, a left side of a vertical bar placed in the middle of the drawing is a result of recognition when the reference data (learning data) is input, while a right side of the vertical bar indicates a result of recognition when the evaluation data is input. As seen from this drawing, the recognition accuracy of the evaluation data is the highest in the "relaxed" state. It can be seen that according to this embodiment, separation and recognition of the emotion is possible. With respect to other emotion, the same result of the recognition accuracy is obtained.

[Experiment 2]

As the device that measures respective changes in oxy-hemoglobin densities and deoxy-hemoglobin densities on a human brain cortex using the near-infrared spectroscopy, the optical topography system ETG-100 manufactured by Hitachi Medical Corporation was used. After being stored in the system ETG-100, measured data was input to a personal computer using removable media and analyzed. A sampling frequency of 10 [Hz] was used, and no particular filtering processing was not performed. Measurement regions are as shown in FIG. 3. Measurement was made in an ordinary environment rather than a sealed room. Subjects were healthy three men of 21 to 24 years old, and the measurement was made in a condition where all the subjects were at rest with their eyes closed.

When the measurement was made, the measurement of the four types of fundamental emotions such as "anger", "sadness", "joy", and "relaxation" was informed to the subjects. The subjects were made to carry out the training that causes the subjects to recall each emotional state. Then, the subjects were made to image emotional states one by one in an order in which the subjects were easy to recall, and to maintain each of the imaged states for three minutes. For first one minute, no recording was performed. Data of subsequent two minutes was recorded, and employed as data used for determining the linear mapping. Then, recording of subsequent one to three minutes (usually two minutes) was performed and used as evaluation data.

Figure 11:
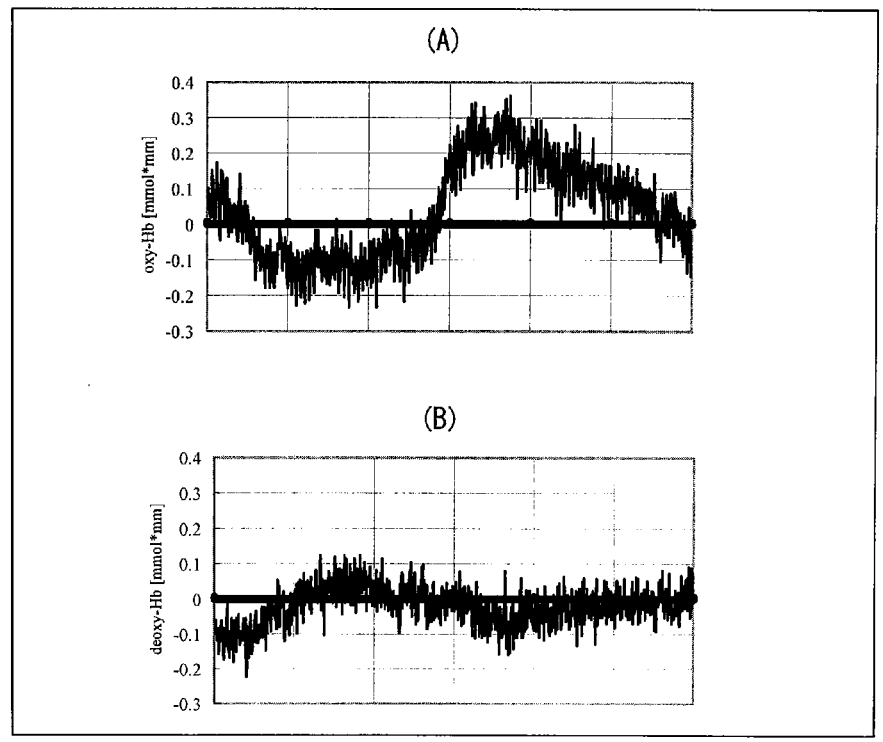
FIG. 11(A) is a diagram showing an example of a graph of a change in a measured oxy-hemoglobin density.
FIG. 11(B) is a diagram showing an example of a graph of a change in a measured deoxy-hemoglobin density.
Figure 12:
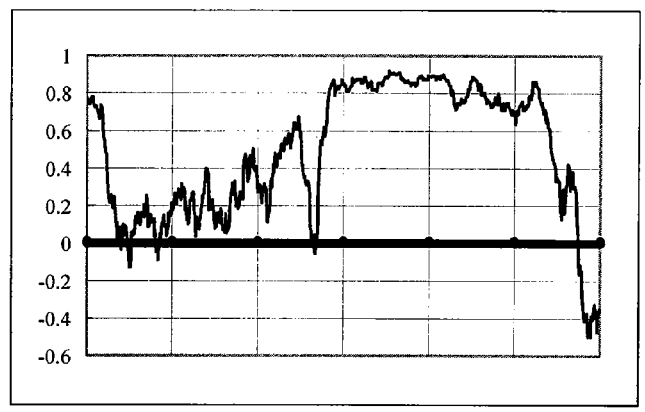
FIG. 12 is a diagram showing an example of a graph of a temporal variation of a correlation-coefficient between channels.

FIG. 11 shows an example of graphs indicating the changes in the measured oxygenated and deoxy-hemoglobin densities, respectively. FIG. 12 shows an example of a graph indicating a temporal variation of a cross-correlation coefficient between the respective channels computed by the expression 1 (expression 1) described before. FIG. 11(A) shows a change in an oxy-hemoglobin density, while FIG. 11(B) shows a change in a deoxy-hemoglobin density. FIG. 12 shows the temporal variation in the cross-relation coefficient between an oxy-hemoglobin density time-variable change amount and a deoxy-hemoglobin density time-variable change amount, measured between channels 1*ch* and 2*ch* when one subject recalls the "anger". In each of the reference data collection step (learning step) and the evaluation data collection step, combinations of 24 channels ($_{48}C_2=1128$) of cross-correlation coefficients were computed for each unit time, thereby obtaining temporal variations in cross-relation coefficients between oxy-hemoglobin density time-variable change amounts and deoxy-hemoglobin density time-variable change amounts as described above. Using results of these computations as the input vector, analysis that determines the linear mapping was performed.

Recognition accuracies of the data used in determination of the linear mapping (recognition accuracies of the reference data for the respective emotions) are shown in the following table 1. Herein, results of three subjects A, B, and C are shown as an example.

TABLE 1

| | Recognition accuracy | | | | |
|---|---|---|---|---|---|
| Subject | Anger | Sadness | Joy | Relaxation | Average Among Emotions |
| A | 99% | 99% | 99% | 100% | 99% |
| B | 99% | 99% | 99% | 100% | 99% |
| C | 100% | 99% | 99% | 100% | 99% |
| Average Among Subject | 99% | 99% | 99% | 100% | 99% |

Figure 13:
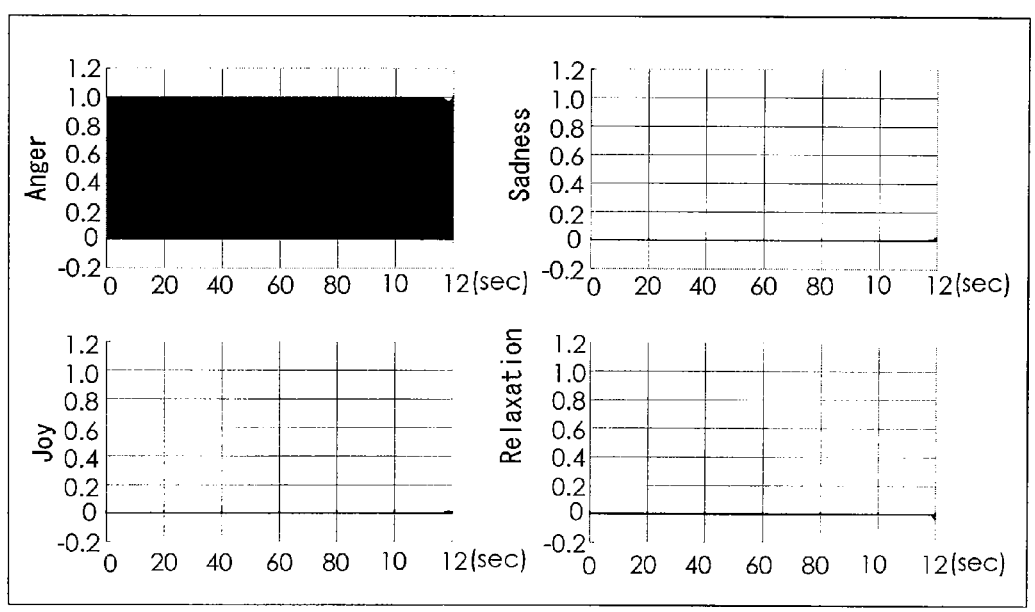
FIG. 13 includes diagrams showing an example of an analysis result of data (learning data) used for determining a linear mapping when "anger" is recalled.

FIG. 13 shows an example of an analysis result of the reference data (learning data) used in the determination of the linear mapping when the "anger" is recalled. As seen from Table 1 and FIG. 13, the recognition accuracies of the evaluation data with respect to the reference data used in the determination of the linear mapping in all the subjects are 99% or more. According to a report described in "Emotion Quantification Using Fractal Dimension Analysis" written by Takahiro Sato and Masahiro Nakagawa, TECHNICAL REPORT OFFICE HIP2002-45, pp. 13-18(2002), when an electroencephalogram is measured in order to measure a brain function, the average recognition accuracy of the learning data used in the determination of the linear mapping by the emotion spectral analysis method is 90%, and 96% by the emotion fractal-dimension analysis method. It can be confirmed from these results that the recognition accuracies of four emotional states in this embodiment are improved more than with the conventional methods that use the electroencephalogram.

Next, recognition accuracies of the evaluation data will be shown in Table 2.

TABLE 2

| Subject | Recognition accuracy | | | | |
|---|---|---|---|---|---|
| | Anger | Sadness | Joy | Relaxation | Average Among Emotions |
| A | 78% | 88% | 54% | 97% | 79% |
| B | 64% | 97% | 100% | 84% | 86% |
| C | 65% | 89% | 72% | 80% | 76% |
| Average Among Subject | 69% | 91% | 75% | 87% | 80% |

Figure 14:
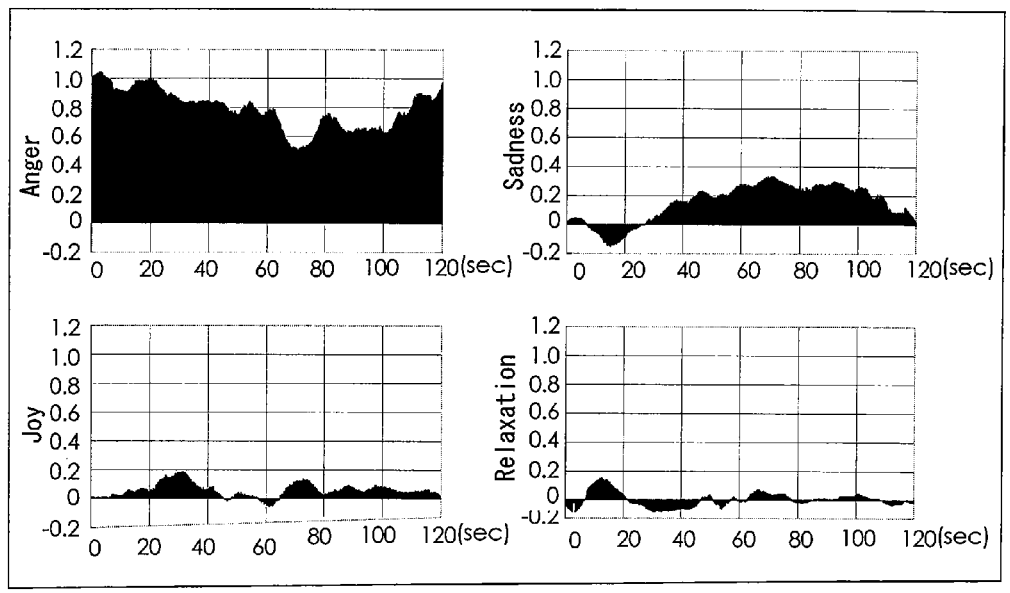
FIG. 14 shows an example of an analysis result of evaluation data.

FIG. 14 shows an example of results of analysis of the evaluation data. According to the report disclosed in the document written by Takahiro Sato and the like described before, the average recognition accuracy of the evaluation data when the evaluation data was recognized using the electroencephalogram and the emotion spectral analysis method is 52%, and the lowest recognition accuracy is 20%. The average recognition accuracy using the electroencephalogram and the emotion fractal-dimension analysis method is 80%, and the lowest recognition accuracy is 48%. On contrast therewith, according to this experiment, it could be confirmed that the average recognition accuracy was 80%, and the lowest recognition accuracy was 54%. It could be confirmed that the method of the present invention had performance that is substantially equivalent to that of the emotion fractal-dimension analysis method which uses the electroencephalogram. Accordingly, it could be confirmed from this experiment that the embodiment described above which measures the hemoglobin densities and utilizes results of the measurement, thereby quantitatively measuring emotional states using the linear mapping determination method can also quantitatively show the emotional states, as in a case where the emotional states are quantitatively measured using the electroencephalogram and the emotion fractal-dimension analysis method.

Incidentally, other determination method such as a neural network may be of course employed as the determination method. As the neural network, a hierarchical neural network or a hierarchical chaos neural network may be employed. In this case, the judging condition may be given to an output layer of the neural network, and the evaluation data may be given to an input layer of the neural network. With respect to the neural network, an example of use of the neural network is shown in each of Japanese Patent Publication No. 05-40840, Japanese Patent Publication No. 06-337852, Japanese Patent Publication No. 08-212275, and Japanese Patent Publication No. 08-235351 as well. A method of using the neural network is known.

Figure 15:
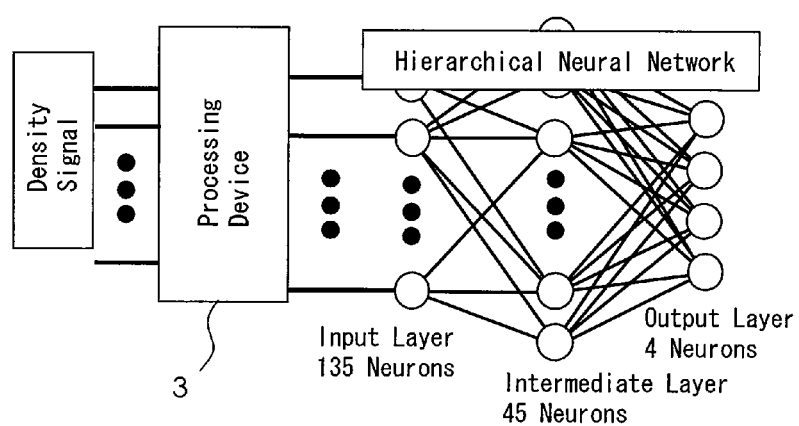
FIG. 15 is a block diagram showing a concept of emotion extraction using a hierarchical neural network.

FIG. 15 is a block diagram showing a concept of emotion extraction by the hierarchical neural network. In this case, the evaluation data is input to the input layer from the preprocessing device 3, and the judging condition is input to the output layer. When the hierarchical neural network as described above is used, the average recognition accuracy of emotion may be increased.

In the embodiment described above, both of the time-variable changes in the oxygenated and deoxy-hemoglobin densities are used. Emotion may also be of course quantitatively measured as in the embodiment described before, using the time-variable changes in only one of the oxygenated and deoxy-hemoglobin densities. The emotional state determination method in this case expressed as a concept is as follows. That is, it is the emotional state determination method in which using the near-infrared spectroscopy, the hemoglobin densities in blood in n measurement regions (in which n is a positive integer) of the human brain cortex of a subject are measured in time series for a predetermined sampling period, respectively, and an emotional state of the subject is determined based on time-variable change data on the measured hemoglobin densities. In the reference data collection step, cross-correlation coefficients of k sets of time-variable change data (in which k is a number obtained by $k = {}_nC_2$) under each of a plurality of types of conditions that influence the emotion are computed for a predetermined unit time. Each of the k sets comprises two of the time-variable change data are selected by permutations and combinations from among time-variable change data on the n hemoglobin densities measured for the respective n measurement regions of the subject. Then, k types of time-variable change patterns of the computed cross-correlation coefficients about the k sets of the time-variable change data are collected as k types of reference data, in advance. Then, in the judging condition determination step, the judging condition necessary for judging the emotional state of the subject by a predetermined judging method is determined from the k types of reference data obtained in the reference data collection step. In the evaluation data collection step, cross-correlation coefficients of the k sets of the time-variable change data under a predetermined condition are computed for the each unit time. Each of the k sets of the time-variable change data comprises two of the time-variable change data which are selected by permutations and combinations from among time-variable change data on the n hemoglobin densities measured for the respective n measurement regions of the subject. Then, k types of time-variable change patterns of the computed cross-correlation coefficients about the k sets of the two-variable change data are collected as k types of evaluation data. Then, in the determination step, the judging condition determined in the condition determination step and the k types of evaluation data are input, thereby quantitatively determining the emotional state of the subject by the predetermined determination method.

INDUSTRIAL APPLICABILITY

According to the present invention, compared with a conventional art, an advantage that an emotional state of a human being may be quantitatively and accurately measured is obtained.

The invention claimed is:

1. An emotional state determination method of measuring at least one of oxy-hemoglobin densities and deoxy-hemoglobin densities in blood of a plurality of measurement regions of a human brain cortex of a subject in time series, respectively, using a near-infrared spectroscopy, and determining an emotional state of the subject based on at least one of time-variable change data on the measured oxy-hemoglobin densities and time-variable change data on the measured deoxy-hemoglobin densities, the method comprising:

in respect of plural sets of the time-variable change data, each of the sets comprising two of the time-variable change data which are selected by permutations and combinations from among the at least one of the time-variable change data on the oxy-hemoglobin densities and the time-variable change data on the deoxy-hemoglobin densities measured for the respective measurement regions of the subject under each of plural types of conditions that influence emotion of the subject, a reference data collection step of computing, for each unit time, cross-correlation coefficients of the plural sets of the time-variable change data, and collecting a plurality of time-variable change patterns of the computed cross-correlation coefficients with respect to the plural sets of the time-variable change data as a plurality of reference data;

a judging condition determination step of determining a judging condition necessary for determining the emotional state of the subject by a predetermined determination method, from the plurality of reference data obtained in the reference data collection step;

in respect of plural sets of the time-variable change data, each of the sets comprising two of the time-variable change data which are selected by the permutations and combinations from among the at least one of the time-variable change data on the oxy-hemoglobin densities and the time-variable change data on the deoxy-hemoglobin densities measured for the respective measurement regions of the subject under a predetermined condition, an evaluation data collection step of computing, for the each unit time, cross-correlation coefficients of the plural sets of the time-variable change data and collecting a plurality of time-variable change patterns of the computed cross-correlation coefficients with respect to the plurality sets of the time-variable change data as a plurality of evaluation data; and a determination step of inputting the judging condition determined in the condition determination step and the plurality of evaluation data, and quantitatively determining the emotional state of the subject by the predetermined determination method.

2. The emotional state determination method according to claim 1, wherein the unit time is a sampling period in the reference data collection step and the evaluation data collection step.

3. The emotional state determination method according to claim 2, wherein the unit time is one second or less.

4. The emotional state determination method according to claim 1, wherein the number of the measurement regions is four or more.

5. The emotional state determination method according to claim 1, wherein as the predetermined determination method, a linear mapping determination method is employed, in the linear mapping determination method, a linear mapping being determined as the judging condition and the plurality of evaluation data being used as an input vector, thereby obtaining a result of determination.

6. The emotional state determination method according to claim 1, wherein as the predetermined determination method, a hierarchical neural network or a hierarchical chaos neural network is employed, the judging condition is given to an output layer of the neural network, and the evaluation data is given to an input layer of the neural network.

7. An emotional state determination method of measuring oxygenated and deoxy-hemoglobin densities in blood of n measurement regions of a human brain cortex of a subject, wherein n being a positive integer, in time series for a predetermined sampling period, respectively, using a near-infrared spectroscopy, and determining an emotional state of the subject based on time-variable change data on the measured oxy-hemoglobin densities and time-variable change data on the measured deoxy-hemoglobin densities, the method comprising:

in respect of m sets of the time-variable change data, wherein m being a number obtained by $m={}_{2n}C_2$, each of the sets comprising two of the time-variable change data which are selected by permutations and combinations from among the n time-variable change data on the oxy-hemoglobin densities and the n time-variable change data on the deoxy-hemoglobin densities for the respective n measurement regions of the subject under each of plural types of conditions that influence emotion, a reference data collection step of computing for each predetermined unit time, cross-correlation coefficients of the m sets of the time-variable change data, and collecting m types of time-variable change patterns of the computed cross-correlation coefficients with respect to the m sets of the time-variable change data as m types of reference data;

a judging condition determination step of determining from the m types of reference data obtained in the reference data collection step a judging condition necessary for determining the emotional state of the subject by a predetermined determination method;

in respect of m sets of the time-variable change data, each of the m sets comprising two of the time-variable change data which are selected by the permutations and combinations from among the time-variable change data on the oxy-hemoglobin densities and the time-variable change data on the deoxy-hemoglobin densities measured for the respective n measurement regions of the subject under a predetermined condition, an evaluation data collection step of computing for the each predetermined unit time cross-correlation coefficients of the m sets of time-variable change data, and collecting m types of time-variable change patterns of the computed cross-correlation coefficients of the m sets of the time-variable change data as m types of evaluation data; and a determination step of inputting the judging condition determined in the condition determination step and the m types of evaluation data, and quantitatively determining the emotional state of the subject by the predetermined determination method.

8. The emotional state determination method according to claim 7, wherein the unit time is one second or less.

9. The emotional state determination method according to claim 7, wherein the number of the measurement regions is four or more.

10. The emotional state determination method according to claim 7, wherein as the predetermined determination method, a linear mapping determination method is employed, in the linear mapping determination method, a linear mapping being determined as the judging method and the plurality of evaluation data being used as an input vector, thereby obtaining a result of determination.

11. The emotional state determination method according to claim 7, wherein as the predetermined determination method, a hierarchical neural network or a hierarchical chaos neural network is employed, the judgment condition is given to an output layer of the neural network, and the evaluation data is given to an input layer of the neural network.

12. An emotional state determination method of measuring hemoglobin densities in blood of n measurement regions of a human brain cortex of a subject, wherein n being a positive integer, in time series for a predetermined sampling period, respectively, using a near-infrared spectroscopy, and determining an emotional state of the subject based on time-variable change data on the measured hemoglobin densities, the method comprising:

in respect of k sets of the time-variable change data, each of the k sets, wherein k being a number obtained by $k={}_nC_2$, comprising two of the time-variable change data which are selected by permutations and combinations from among the time-variable change data on the n hemoglobin densities for the respective n measurement regions of the subject under a plurality of conditions that influence emotion, a reference data collection step of computing for each predetermined unit time, cross-correlation coefficients of the k sets of the time-variable change data and collecting k types of time-variable change patterns of the cross-correlation coefficients with respect to the k sets of the time-variable change data in advance as k types of reference data;

a judging condition determination step of determining from the k types of reference data obtained in the reference data collection step a judging condition necessary for judging the emotional state of the subject by a predetermined determination method;

in respect of k set of the time-variable change data, each of the sets comprising two of the time-variable change data which are selected by the permutations and combinations from among the time-variable change data on the hemoglobin densities for the respective n measurement regions of the subject under a predetermined condition, an evaluation data collection step of computing for the each unit time, cross-correlation coefficients of the k sets of the time-variable change data, and collecting k types of time-variable change patterns of the computed cross-correlation coefficients with respect to the k sets of the time variable change data, as k types of evaluation data; and a determination step of inputting the judging condition determined in the condition determination step and the k type of evaluation data, and quantitatively determining the emotional state of the subject by the predetermined determination method.

13. The emotional state determination method according to claim 12, wherein the hemoglobin densities are deoxy-hemoglobin densities or oxy-hemoglobin densities.

14. The emotional state determination method according to claim 12, wherein the unit time is one second or less.

15. The emotional state determination method according to claim 12, wherein the number of the measurement regions is four or more.

16. The emotional state determination method according to claim 12, wherein as the predetermined determination method, a linear mapping determination method is employed, in the linear mapping determination method, a linear mapping being determined as the judging condition and the plurality of evaluation data being used as an input vector, thereby obtaining a result of determination.

17. The emotional state determination method according to claim 12, wherein as the predetermined determination method, a hierarchical neural network or a hierarchical chaos neural network is employed, the judgment condition is given to an output layer of the neural network, and the evaluation data is given to an input layer of the neural network.

* * * * *